Figure 2:
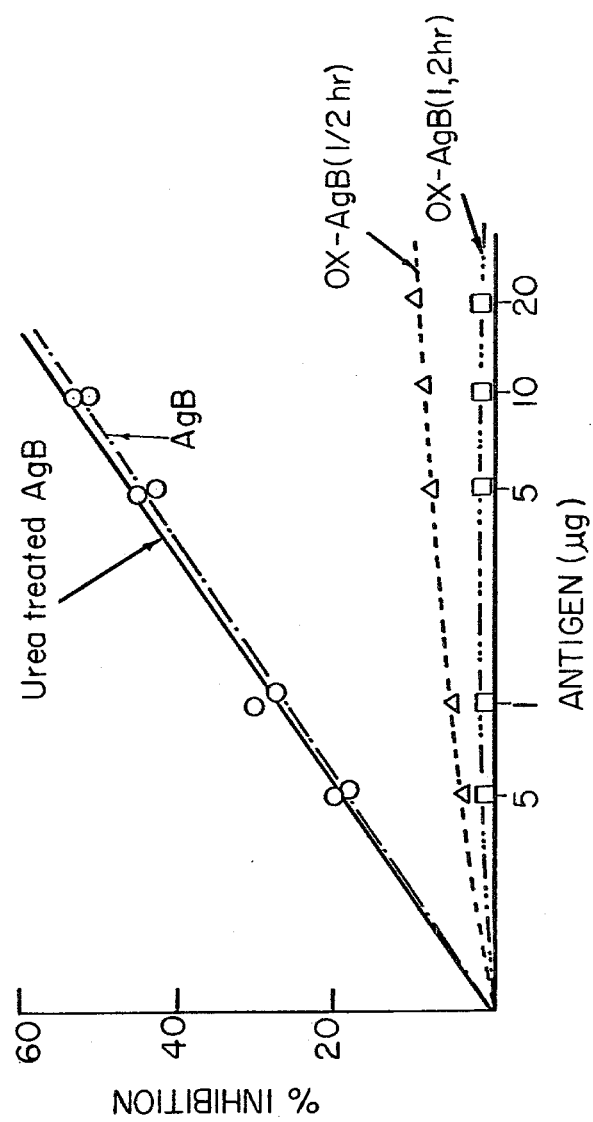

United States Patent [19]

Malley

[11] 4,256,732

[45] Mar. 17, 1981

[54] MODIFIED GRASS POLLEN ANTIGENS

[75] Inventor: Arthur Malley, Beaverton, Oreg.

[73] Assignee: Research Corporation, New York, N.Y.

[21] Appl. No.: 78,813

[22] Filed: Sep. 25, 1979

Related U.S. Application Data

[62] Division of Ser. No. 933,907, Aug. 15, 1978.

[51] Int. Cl.³ .............................................. A61K 39/36
[52] U.S. Cl. ................................. 424/91; 260/112 R; 260/112.5 R
[58] Field of Search ........................ 260/112 R, 112.5; 424/91

[56] References Cited

U.S. PATENT DOCUMENTS

| | | | |
|---|---|---|---|
| 4,140,679 | 2/1979 | Malley | 260/121 X |
| 4,158,705 | 6/1979 | Malley | 424/91 |

OTHER PUBLICATIONS

Malley et al., *Immunochemistry*, vol. 12, pp. 551–554 (1975).
Girard et al., *Chem. Abstracts*, vol. 83, 162003u (1975).
Malley et al., *J. of Immunology*, vol. 99, No. 4 (1967), pp. 825–830.
Malley et al., *Chem. Abstracts*, vol. 83, 161,957w (1975).
Sanderson et al., *Immunology*, vol. 20 (1971), pp. 1061–1065.
Axen et al., *Nature*, vol. 214 (1967), pp. 1302–1304.
Malley et al., *J. of Allergy*, vol. 43, No. 2 (1969), pp. 59–64.

*Primary Examiner*—Howard E. Schain
*Attorney, Agent, or Firm*—Kerkam, Stowell, Kondracki & Clarke

[57] ABSTRACT

Oxidative rearrangement and cleavage of hydroxy aromatic rings of quercitin moiety of Timothy grass pollen antigen or antigenic fragments gives rise to a modified antigen having no antigenic properties but retaining capability of activating T-cells for regulation of immune response.

The invention includes the modified antigens, the method of oxidative cleavage, immunotherapeutic methods for alleviating allergic responses to the Timothy grass pollen antigens and immunotherapeutic compositions therefor.

14 Claims, 4 Drawing Figures

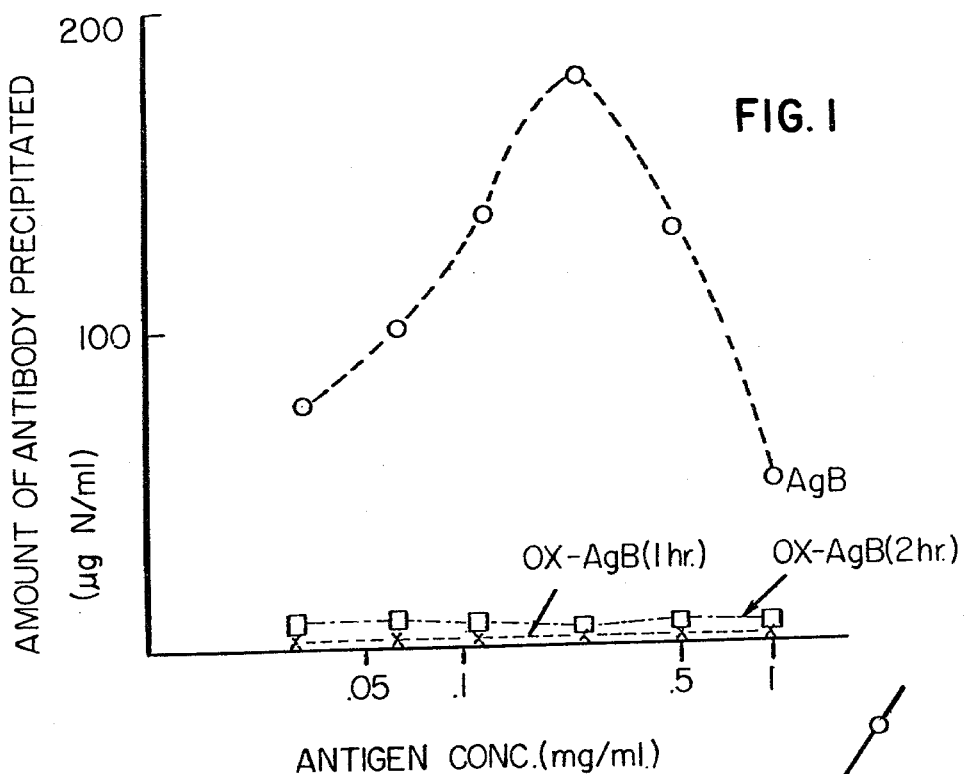
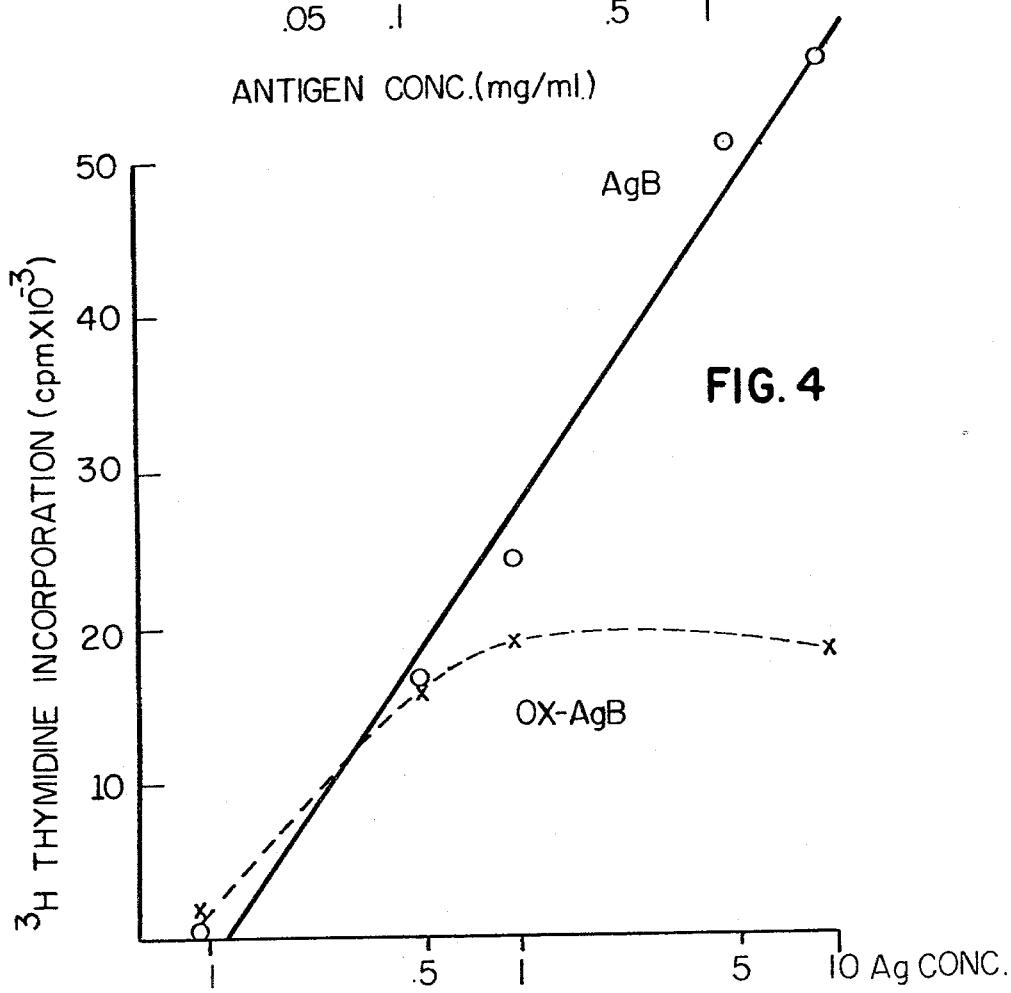

MODIFIED GRASS POLLEN ANTIGENS

This is a division, of application Ser. No. 933,907, filed Aug. 15, 1978.

BACKGROUND OF THE INVENTION

Recent studies have resulted in a characterization of the antigenic determinant of antigen B of Timothy grass pollen. The antigen is composed of a flavanoid pigment, quercitin; a disaccharide, cellobiose; and a polypeptide "tail". Antigen B is the generic name for mixtures containing two or more antigen fragments conventionally termed "antigen D, $D_1$, $D_2$, $D_3$, etc. They differ from each other in the length of the polypeptide "tail". In antigen $D_3$, the "tail" consists of a single aminoacid, namely, threonine. See Malley et al, *Dev. Biol. Stand.*, 1975, 29 (Int. WHO-IABS, Symp. Stand. Control Allergens Adm. Man., 1974), 29–40; Kramer-Kleinert et al, *Dev. Biol. Stand.*, 1975, 29 (Int. WHO-IABS, Symp. Stand. Control Aller- gens Adm. Man., 1974), 188–96; Malley et al, *Immunochemistry*, 1975, Vol. 12, pages 551–554; Malley et al, *Journal of Allergy*, Vol. 43, No. 2, February, 1969, pages 59–64; Gerard et al, *Immunochemistry*, 1975, Vol. 12, pages 545–9; Malley et al, *Journal of Immunology*, Vol. 99, No. 4 (1967), pages 825–830; Sanderson et al, *Immunology*, Vol. 20 (1971), pages 1061–1065; and Axen et al, *Nature*, Vol. 214 (1967), pages 1302–1304.

In co-pending application Ser. No. 731,414, filed Oct. 12, 1976, now U.S. Pat. No. 4,140,679 it is disclosed that the various antigen D fragments coupled to various proteins or peptides through the free carboxyl group of threonine initiate significant histamine release from sensitized tissue. It is further disclosed therein, however, that these same antigen D fragments coupled to various proteins and peptides through the sugar moiety give rise to a dose-dependent inhibition of histamine release from sensitized tissue.

These studies intimate strongly that quercitin represents the major portion of the antigenic determinant of antigen B.

Antigen B and its various fragments may be represented by the structural formula:

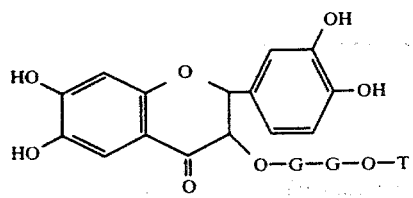

wherein G represents glucose and T represents threonine or a peptide linked to said structure through the threonine molecule.

Antigen $D_1$ has the structure set forth above wherein the peptide tail is such that the molecular weight is about 5,000. Antigen $D_2$ has a molecular weight of about 2,500. In antigen $D_3$, T is threonine alone.

The quercitin fraction of the antigen structure is linked to the glucose moieties via an ether linkage through OH groups on the respective molecules. The threonine linkage to the glucose moiety is also an ether linkage through an OH group on the cellobiose fraction and the OH group of threonine.

The nature of the allergic reaction or response in humans and animals is not completely understood. It is theorized that the allergic response to a foreign antigen, such as the antigen of grass pollen, involves the interaction of at least two different cell types. One of these is conventionally termed a T-cell, or Thymus derived lymphocyte, and the second a B-cell, which is a bone marrow derived lymphocyte. Each of these two cells, the T and the B lymphocytes, recognize different parts of the protein that causes the allergic response. The B-lymphocyte recognizes the antigenic determinant whereas the T-lymphocyte recognizes a different portion of the protein, termed a carrier determinant. To achieve suppression of the immune response involved in allergic diseases one can attack the problem by either suppressing the formation of antibody by blocking B-cell differentiation or by affecting the T-cell population. The B-lymphocyte actually produces the antibody. T-cells do not produce the circulating antibody that is involved in allergic disease, but regulate their production. One sub-population of T-cells which assists in making antibodies are the so-called helper T-cells. They effectively cooperate or interact with the B-lymphocyte to produce antibodies. Another sub-population of T-cells, the "suppressor" T-cell or $T_s$ cell, effectively suppresses the action of helper T-cells so that they cannot participate with B-lymphocytes to produce antibodies.

It is an object of the present invention to provide a method for modifying the antigenic properties of Timothy antigen B and/or its various fragments to yield a product devoid of antigenic properties but capable of activating T-cells.

SUMMARY OF THE INVENTION

The present invention is predicated on the discovery that subjecting the quercitin moiety of grass pollen antigen having the structure:

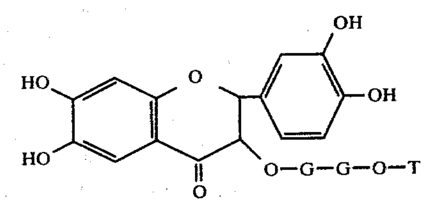

wherein: G represents glucose and T represents threonine or a peptide linked to the structure through a threonine molecule to oxidative conditions such that the dihydroxy aromatic rings of the quercitin moiety undergo rearrangement and ring scission yield a product substantially devoid of antigenic properties but capable of activating T-cells and inducing $T_s$ cells.

DETAILED DESCRIPTION OF THE DRAWINGS

FIGS. 1–4 represent graphic illustrations of the antigenic properties of the oxidatively modified antigen of the present invention.

DETAILED DESCRIPTION OF THE INVENTION

The method of the invention is applicable to any quercitin moiety containing antigen or antigen fragment such as antigen B, antigen D, antigen $D_1$, $D_2$, $D_3$, etc.

The method gives rise to a modified antigen which may be compounded in unit dosage form to provide an immunotherapeutic composition for inhibiting allergic reactions in humans and animals sensitive to the said antigens.

It is known that hydroxy aromatic rings are subject to oxidative scission following rearrangement thereof, depending upon the reaction conditions. It is also known that certain oxidations affect a variety of ammino acids in different ways. It is known that tyrosine and methionine are present in the polypeptide "tail" of antigens B or D. It is further known that oxidative conditions sufficiently rigorous to effect ring scission in the quercitin moiety will also affect the tyrosine and methionine content of the polypeptide "tail". It has been found, however, that modification of these two residues and a minimum of other amminoacid residues present in the tail will not affect the capability of the modified antigen to induce active T-cells.

Any oxidation reaction capable of effecting rearrangement and ring scission of the hydroxy aromatic rings of the quercitin moiety, while not substantially modifying the polypeptide "tail", will result in a product having substantially no antigenic properties but retaining its capability of activating T-cells and inducing $T_s$ cells.

Photooxidative cleavage of the hydroxy aromatic rings has been found to be highly effective in producing the modified antigen of the invention. Obviously, the rate of oxidation and the residues affected depend upon many variables, including the pH, concentration of the photosensitizer, the size of the vessel and the intensity and duration of exposure of the sample to light.

It is to be understood, however, that any oxidative procedure which results in rearrangement and scission of the hydroxyaromatic rings of quercitin in the antigen or fragments thereof while avoiding substantial modification of the peptide tail may be employed according to the present invention.

Thus, chloramine-T [sodium para-toluenesulfonchloramine], lactoperoxidase and potassium permanganate may also be employed as suitable oxidizing agents for modification of the quercitin moiety of the antigen or antigen fragments.

EXAMPLE 1

Timothy pollen extract (WST) and purified antigen B, AgB, were prepared as described by Malley et al, (*J. Immunol.* 99, 825 (1967). The protein concentration of these antigen preparations was determined by nesslerization (Campbell et al., *Methods in Immunology,* Ed. W. A. Benjamin, N.Y., pg. 53, 1963).

The AgB was treatred with 8 M urea, as described by Takatsu and Ishizaka (*Cell Immunol.,* 20, 276, 1975), i.e., two grams of urea were added to 2.5 ml of a 1% solution of AgB in 0.1 M Tris-HCl buffer (pH 8.0). After 18 hr. of incubation at room temperature, the protein solution was dialyzed against phosphate-buffered saline, concentrated back to its original volume (2.5 ml) by negative pressure, and tested for its reagin-binding activity by the radioallergosorbent (RAST) inhibition method.

Photooxidation of Antigen B

Three milligrams of AgB (0.4 ml) and 2 ml of 0.2 M phosphate buffer (pH 9) were added to 10-ml serum vials. The vials were covered with aluminum foil so that no light would get in. One-half millimeter of methylene blue photosensitizer 0.2 mg/ml in 0.2 M phosphate buffer (pH 9), was added to each vial, and the reaction mixture was saturated with $O_2$ by a gentle bubbling of the gas into the solution for 8 to 10 min. The serum vials were stoppered immediately and incubated at 37° C. for 30 min. The aluminum foil was removed from the vials, and their contents were exposed to two 150-watt lights positioned 1.5 inches from the vials for varying periods of time at 37° C. The samples were removed from the vials and dialyzed against distilled water in Spectropor membranes (6000 to 8000 molecular-weight pore size) (Spectrum Medical Industries, Inc., Los Angeles, Calif.) for 48 hrs.

Amino Acid Analysis

Two-milligram samples of AgB and photooxidized antigen B (OX-AgB) (0.5 hr., 1 hr., and 2 hr. photooxidation) were lyophilized to dryness in Pyrex digestion tubes (13×100 mm). Each sample was re-suspended in 5.7 N HCl and treated with nitrogen gas: the gas was bubbled into each tube for 10 min.; then each tube was sealed by an oxygen torch and heated at 110° C. for 20 hrs. Amino acid analysis of each sample was performed by the method of Spackman et al (*Anal. Chem.,* 30, 1190, 1958) with a Beckman model 120C amino acid analyzer. The tryptophan content was determined by the method of Spies and Chambers (*Anal. Chem.,* 21, 1249, 1949). The results are set forth in Table 1:

TABLE 1

EFFECT OF PHOTOOXIDATION UPON THE AMINO ACID COMPOSITION OF ANTIGEN B

| Amino Acid Residue | Native AgB[a] (M/mole) | OX-AgB 0.5 hr. | 1 hr. | 2 hr. |
|---|---|---|---|---|
| Aspartic | 7 | 7 | 7 | 7 |
| Glutamic | 8 | 8 | 8 | 8 |
| Threonine | 5 | 5 | 5 | 5 |
| Serine | 4 | 4 | 4 | 4 |
| Proline | 4 | 4 | 4 | 4 |
| Glycine | 3 | 3 | 3 | 3 |
| Alanine | 14 | 14 | 14 | 14 |
| Valine | 5 | 5 | 5 | 5 |
| Methionine | 1 | .5 | trace | trace |
| Isoleucine | 2 | 2 | 2 | 2 |
| Leucine | 4 | 4 | 4 | 4 |
| Phenylalanine | 3 | 3 | 3 | 3 |
| Tyrosine | 2 | 0 | 0 | 0 |
| Tryptophan | 6 | 3 | 3 | 3 |
| Lysine | 6 | 6 | 6 | 6 |
| Histidine | 1 | 1 | 1 | 1 |
| Total number of residues | 75 | 69.5 | 69 | 69 |

[a]Numbers represent the $\frac{\mu\text{Moles of amino acid}}{\text{mole of protein}}$ and are rounded off to the nearest whole integer.

Antisera

Rabbit anti-WST serum, prepared as previously described (Malley et al, supra, 1967), contained 1.1 mg of antibody protein/ml directed against AgB. Human reaginic serum directed against timothy pollen antigens was obtained from 50 patients and pooled (5 ml from each). This pool had a Prausnitz-Kuestner (P-K) titer of 1:2500.

Precipitation Analysis

Rabbit anti-WST serum (0.5 ml) was added to 0.5 ml of varying concentrations (0.03 to 1 mg of protein) of either AgB or OX-AgB. The mixtures were incubated at 37° C. for 30 min. and at 4° C. for 48 hrs. The precipitates were washed three times with 0.01 M cacodylic saline buffer (pH 7) and air-dried; the dried precipitates were quantified as described by Campbell et al., supra, p. 136. The protein content of each precipitate was determined by nesslerization (Campbell et al., supra, pg. 53). The results are depicted in FIG. 1. The values reported represent the mean of duplicate assays.

Passive Transfer Tests

Diluted pooled serum (0.1 ml) was intradermally injected at various sites into the skin of a nonallergic volunteer, and 48 hr. later each site was challenged with 0.025 ml of AgB (0.1 µg of protein/ml). Reactions were read 30 min. later and were graded as follows: negative, —; 5- to 10-mm wheal, +; 10- to 15 mm wheal, 2+; 15- to 20-mm wheal, 3+; and greater than 20-mm wheal, 4+.

The results are set forth in Table 2:

TABLE 2

PASSIVE TRANSFER REACTIVITY OF NATIVE AND PHOTOOXIDIZED ANTIGEN B WITH A POOL OF HUMAN ANTITIMOTHY SERA

| Antigen | Protein con. (µg/ml) | P-K Rections[a] | | | | |
|---|---|---|---|---|---|---|
| | | 1:100 | 1:200 | 1:400 | 1:800 | 1:1000 |
| AgB | 0.1 | 4+ | 4+ | 3+ | 3+ | 2+ |
| OX-AgB[b] | 10.0 | — | — | — | — | — |

[a]A serum pool from 50 patients sensitive to timothy grass pollen was used in these experiments; the average P-K titer of this serum was 1:2500. Serum diluted (0.1 ml) was intradermally injected at various sites into the skin of a nonallergic human volunteer. Each site was challenged with .025 ml of antigen 48 hrs. later.
[b]The 1-hr. and 2-hr. samples.

Radioallergosorbent Inhibition

Two grams of Whatman 3 MM paper disks (3 mm in. diameter) were activated with CNBr by the method of March et al. (*Anal. Biochem.*, 60, 149, 1974). The activated disks were washed with 500 ml of cold 0.1 M NaHCO$_3$-saline buffer (pH 9) on a sintered glass filter, and the moist disks were added to 30 ml of a WST solution (1 mg of protein/ml) in 0.1 M NaHCO$_3$-saline buffer (pH 9). This mixture was stirred for 36 hr. at 4° C. and washed with 500 ml each of the following cold reagents: 0.2 M Na$_2$CO$_3$, 2 M urea, 0.2 M NaAc, and 0.1 M phosphate-buffered saline, pH 7.2. The WST-coated disks were stored in phosphate-buffered saline at 4° C. until used.

One-tenth of a milliliter of human reaginic serum diluted 1:37.5 (P-K titer of 10,000) from a timothy-sensitive patient was incubated with 0.1 ml of varying concentrations (0.5 to 20 µg of protein) of either AgB or OX-AgB for 45 min. at 37° C. The WST-coated disks were blotted dry, and one disk was added to each mixture of preincubated reagin. After 6 hr. of incubation at room temperature, each disk was washed three times (3×5 ml), and 5000 to 8000 cpm of $^{125}$I-anti-IgE was added to each disk. The mixtures were incubated for 16 hr. at 4° C. The WST-coated disks were washed four times (4×5 ml) with RAST buffer and counted by a Packard scintillation counter (Packard Instrument Company, Inc., Downers Grove, Ill.). Twenty to thirty percent of the $^{125}$I-anti-IgE added was bound to disks when the reaginic serum was preincubated with normal human serum. The percent of inhibition achieved by AgB and OX-AgB was obtained with the following equation:

$$\text{Percent of Inhibition} = (1 - \frac{RAST \text{ counts with added fraction}}{RAST \text{ counts without fraction}}) \times 100$$

The results are depicted in FIG. 2. The values reported represent the means of duplicate assays.

Immunizations

Figure 3:
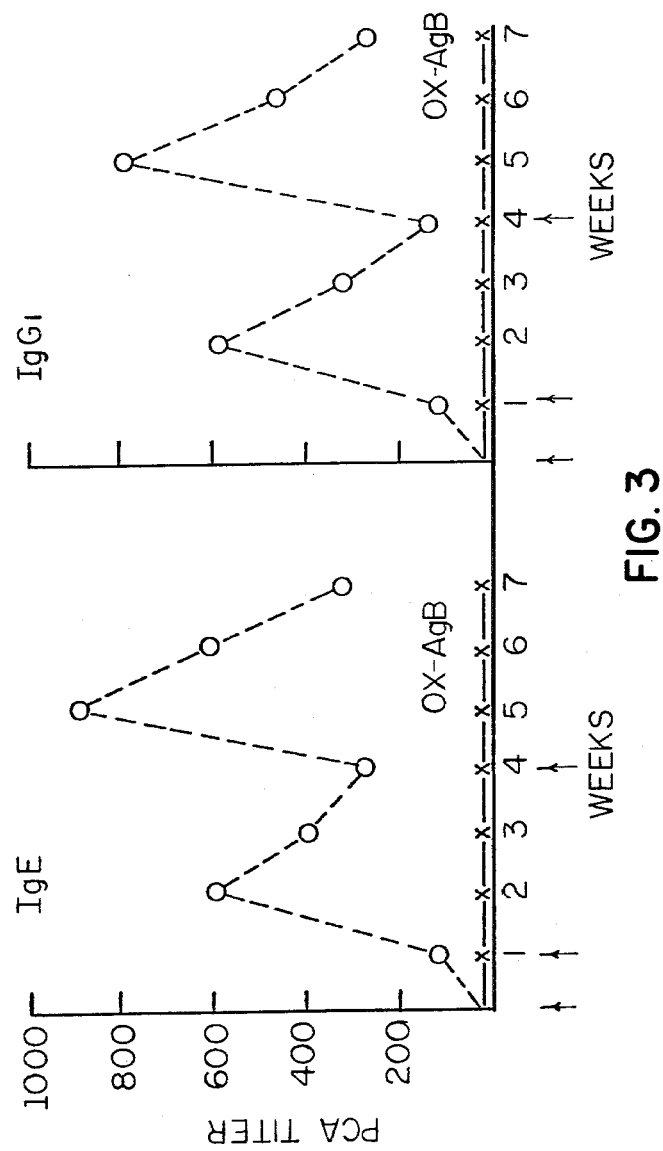

LAF$_1$ mice (Jackson Laboratories, Bar Harbor, Maine) were immunized with WST as previously described (Fairchild et al., *J. Immunol.* 115, 446, 1975). The immunogenicity of OX-AgB was studied by immunization of LAF$_1$ mice with OX-AgB (10 to 100 µg) adsorbed to aluminum hydroxide (Levine et al., *Int. Arch. Allergy*, 39, 156, 1970). Animals were immunized with OX-AgB at weekly intervals for 2 weeks and given another boost with OX-AgB 3 weeks later. Blood samples were collected 7 days after the initial injections, 7, 10, and 14 days after the second injections; and 7, 10, and 14 days after the final injections of OX-AgB. The serum IgG$_1$ and IgE titers of immunized mice were measured by passive cutaneous anaphylaxis as previously described (Fairchild et al. supra.) The results are depicted in FIG. 3. The titers reported represent the mean value obtained in at least two animals with a pool of serum from at least 5 mice. The arrows indicate when the mice were immunized with AgB or OX-AgB.

Photooxidation converted the yellow-pigmented AgB to a colorless material with a corresponding decrease in the optical density at 280 nm. A comparison of the amino acid composition of AgB and several OX-AgB samples (Table 1) shows a complete reduction in the tyrosine content of OX-AgB and a decrease in the methionine and tryptophan contents; however, the other amino acids remained relatively unchanged, a fact that suggests the polypeptide structure of AgB was not significantly altered by photooxidation.

The effect of photooxidation upon the antigenic determinants of AgB was evaluated by comparing AgB and Ox-AgB for their ability (1) to precipitate rabbit antibody against AgB, (2) to initiate P-K reactions in skin of a nonallergic individual passively sensitized with IgE-containing serum from timothy-sensitive patients, and (3) to inhibit specific IgE binding to WST-coated paper disks in the RAST assay.

Rabbit anti-timothy serum containing 1.1 mg of antibody protein/ml against AgB failed to yield precipitable antibody with OX-AgB (0.5-hr., 1-hr., and 2-hr. samples) (FIG. 1).

Table 2 shows that AgB (2.5 ng) induced strong P-K reactions even at a 1:1000 dilution of the reagin pool. In contrast, a concentration of OX-AgB (1-hr. and 2-hr. samples) 100 times greater (250 ng) than the AgB concentration used failed to initiate allergic skin reactions in the skin of the nonallergic volunteer.

The ability of OX-AgB to inhibit binding of $^{125}$I-anti-IgE with timothy reagin was further evaluated by comparing AgB and OX-AgB inhibition of binding in a RAST assay for timothy reaginic antibodies (FIG. 2). In these studies, AgB gave a linear dose-dependent inhibition of $^{125}$I-anti-IgE binding to IgE-bound WST-coated paper disks, but OX-AgB (1-hr. and 2-hr. samples) failed to inhibit $^{125}$I-anti-IgE binding even at a 20 µg concentration. In contrast, urea-treated AgB gave a dose-dependent inhibition of $^{125}$I-anti-IgE-bound WST-coated disks identical to that of native AgB.

Another way to evaluate the effect of photo-oxidation upon the antigenic determinant of AgB is to compare the immunogenic properties of native and OX-AgB. LAF$_1$ mice in groups of five animals were immunized with either 10 μg of AgB protein or 10 to 100 μg of OX-AgB protein (1-hr. sample). Mice immunized with AgB made significant levels of IgG$_1$ and IgE antibody after a second and third injection of AgB. In contrast, mice immunized by the same immunization schedule with 10 or 100 μg of OX-AgB protein did not produce either IgG$_1$ or IgE antibody that reacted with AgB or OX-AgB (FIG. 3).

Antigen-induced lymphocyte transformation was used to compare the relative T-cell-activating properties of AgB and OX-AgB. See FIG. 4 wherein the reported values represent the mean of quadruplicate assays (individual assays vary less than 10% from the means). Over the concentration range tested (0.1 to 10 μg of protein), AgB gave a dose dependent increase in Ag-induced proliferation of immune LAF$_1$ mice spleen cells. On the other hand, OX-AgB (1-hr. to 2-hr. samples) had a peak response at 1 μg that apparently plateaued at this level over the remainder of the concentrations of OX-AgB tested. These data indicate that OX-AgB retains a significant amount of Ag-induced proliferative capabilities of native AgB.

Photooxidation of AgB results in a complete loss in the ability of OX-AgB to react with either rabbit anti-AgB (FIG. 1) or human IgE antibodies (Table 2, FIG. 2) directed against the antigenic determinants on AgB. Complete acid hydrolysis of OX-AgB indicated that the only significant modification of native AgB was to the quercitin and tyrosine moieties (Table 2). Attempts to modify the antigenic determinant of AgB by denaturation with 8 M urea were unsuccessful since native and urea-treated AgB had identical dose-response curves for $^{125}$I-anti-IgE binding to IgE- bound antigen-conjugated paper disks (FIG. 2). These data, taken together with data from earlier studies (Malley at al., 1975a, 1975b, 1978) suggest that the major part of the antigenic determinant of AgB is not dependent upon its three-dimentional polypeptide structure, but is dependent upon the presence of the pigment quercitin in the antigen molecule.

A number of studies (Takatsu et al., Cell Immunol., 20, 276, 1975; Scibienski et al., J. Exp. Med., 136, 1308, 1972; Turkin et al., Proc. Natl. Acad. Sci., 74, 3984, 1977) have suggested that determinants recognized by T and B cells may differ. The B cell receptors combine with haptenic determinants, and T cell receptors are activated by interaction with carrier determinants on the antigen. The above example clearly indicates that OX-AgB neither combines with IgG$_1$ or IgE antibodies nor induces the production of antibody against AgB, a fact that suggests OX-AgB does not prime B cells specific for the native antigen. Previous studies (Fairchild et al., J. Immunol., 117, 2137, 1976) indicated that the AgB-induced proliferative response of mice immunized with AgB was due to both T and B cells. The carrier determinant on Ox-AgB retains a substantial portion (>40%) of the proliferative response of immune spleen cells to AgB (FIG. 3). The above example indicates that the carrier determinant of OX-AgB activates T cells primed with native AgB.

EXAMPLE 2

The following procedure may be employed to oxidatively modify an antigen with chloramine T:

Protein (1 to 5 mg) is dissolved in 4 ml of 0.05 M phosphate buffer, pH 7. The protein solution is placed in a 30 ml beaker and stirred by a magnetic stirrer. The beaker is placed in a large plastic dish filled with ice to keep the reactants cold. Chloramine T (100 μg to 5 mg) dissolved in 0.05 M phosphate buffer, pH 7, is added dropwise and mixed for varying periods of time. To stop the reaction an equal weight of sodium metabisulfite is added to neutralize any remaining oxidizing agent. Excess reagents are removed by passage of the solution over a Sephadex G25 column equilibrated in H$_2$O. The breakthrough peak containing the protein is collected and lyophilized.

EXAMPLE 3

The following procedure may be utilized to oxidatively modify an antigen with lactoperoxidase.

Protein (1 to 5 mg) is dissolved in 4 ml of 0.01 M phosphate-buffered saline, pH 7.2. 200 μg of lactoperoxidase, and 25 μl of 0.03 to 0.1% H$_2$O$_2$ are added. The reaction mixture is incubated at 37° C. for 10 to 20 minutes, during which time two more 25 μl aliquots of H$_2$O$_2$ were added. The reaction was terminated by the addition of 10 volumes of cold 5 mM L-cysteine-HCl in phosphate-buffered saline. The protein was recovered by passage of the mixture over a Sephadex G75 column. The enzyme is not held up by the Sephadex G75 while antigen B is retarded by the matrix. Elution of this material is accomplished by continued washing of the column with buffer. The eluted protein is concentrated by lyophilization.

What is claimed is:

1. An immunotherapeutic method for treating grass pollen allergies comprising administering to an individual an amount of a modified grass pollen antigen sufficient to induce suppressor T-cells that will result in a suppression of allergic antibodies to grass pollen antigen, said modified antigen being the product of a method comprising subjecting a quercitin moiety containing grass pollen antigen or fragment thereof having the structure:

![structure showing HO and OH substituted aromatic rings connected via O linkages with O-G-G-O-T chain]

wherein:

G represents glucose, and

T represents threonine or a poly-peptide linked to said structure through a threonine molecule; to oxidative conditions such that the said dihydroxy aromatic rings undergo rearrangement and ring scission without substantially modifying said threonine or polypeptide to yield a product substantially devoid of antigenic properties but capable of activating T-cells and inducing T$_s$ cells.

2. The method of claim 1 wherein said grass pollen antigen is antigen B, antigen D, antigen D$_1$, antigen D$_2$, or antigen D$_3$.

3. The method of claim 1 wherein said oxidative conditions also result in the rearrangement and ring scission of the hydroxy aromatic ring present in the tyrosine moiety of said poly-peptide T.

4. The method of claim 1 wherein the extent of said oxidation is sufficient to result in a modified antigen incapable of reacting with antibodies directed against the antigenic determinant structure of said starting antigen.

5. The method of claim 4 wherein said oxidative conditions are such that substantial modification of the amino acid content of said antigen is avoided.

6. The method of claim 1 wherein said grass pollen is photooxidized.

7. The method of claim 6 wherein said photo